US009033706B2

United States Patent
Lee et al.

(10) Patent No.: US 9,033,706 B2
(45) Date of Patent: May 19, 2015

(54) WIRELESS RECHARGER OF COMPLETE MELTING TYPE FOR ENDODONTIC TREATMENT

(75) Inventors: In-Whan Lee, Seoul (KR); Cheol-Su Kim, Incheon (KR); Seung-Ho Baek, Seoul (KR)

(73) Assignee: B & L BIOTECH CO., LTD., Gyeonggi-do (KR)

( * ) Notice: Subject to any disclaimer, the term of this patent is extended or adjusted under 35 U.S.C. 154(b) by 538 days.

(21) Appl. No.: 11/909,935

(22) PCT Filed: Feb. 27, 2006

(86) PCT No.: PCT/KR2006/000676
§ 371 (c)(1),
(2), (4) Date: Jan. 18, 2008

(87) PCT Pub. No.: WO2006/104314
PCT Pub. Date: Oct. 5, 2006

(65) Prior Publication Data
US 2008/0187883 A1 Aug. 7, 2008

(30) Foreign Application Priority Data
Mar. 28, 2005 (KR) .................. 10-2005-0025672

(51) Int. Cl.
*A61C 5/04* (2006.01)
(52) U.S. Cl.
CPC .. *A61C 5/04* (2013.01); *A61C 5/045* (2013.01)
(58) Field of Classification Search
CPC .......... A61C 5/04; A61C 5/045; A61C 5/062; A61C 19/004; H05B 2203/03; H05B 33/0815; H05B 33/0842
USPC .......... 433/80, 81, 89, 90; 219/221, 227, 229, 219/241; 374/141, 179; 138/149; 165/136; 362/294

See application file for complete search history.

(56) References Cited

U.S. PATENT DOCUMENTS

| | | | | |
|---|---|---|---|---|
| 3,624,907 A | * | 12/1971 | Brass et al. | 433/81 |
| 4,072,316 A | * | 2/1978 | Decker et al. | 277/597 |
| 4,185,439 A | * | 1/1980 | Bischlipp et al. | 52/843 |
| 4,429,213 A | * | 1/1984 | Mathieu | 392/468 |
| 4,472,141 A | | 9/1984 | Dragan | |
| 5,324,273 A | * | 6/1994 | Discko, Jr. | 604/240 |

(Continued)

OTHER PUBLICATIONS

International Search Report (PCT/ISA/210), Issued on May 26, 2006, International Application No. PCT/KR2006/000676.

*Primary Examiner* — Cris L Rodriguez
*Assistant Examiner* — Matthew Nelson
(74) *Attorney, Agent, or Firm* — IP Legal Services, LLC (57) ABSTRACT

A complete melting type cordless filling instrument for endodontic treatment is disclosed which uses a switching circuit, to be operable using a miniature dry battery for supplying DC power. The filling instrument includes a body with a battery for supplying DC power, a heater at a front end of the body to heat and melt gutta-percha, an injector mounted to the body in front of the heater to discharge the melted gutta-percha, a charging part provided at the body to charge the gutta-percha in the body, a feeding member which feeds the gutta-percha charged in the body, a filling switch which turns on the heater, and a control circuit installed in the body, to control a temperature of the heating core and an operation of the heating core. The control circuit includes the filling switch, and a switching circuit adapted to efficiently maintain electrical energy supplied from the battery.

11 Claims, 10 Drawing Sheets

(56) References Cited

U.S. PATENT DOCUMENTS

| | | | | |
|---|---|---|---|---|
| 5,837,973 A * | 11/1998 | Tamura | | 219/241 |
| 6,168,432 B1 * | 1/2001 | Marlin | | 433/81 |
| 6,696,643 B2 * | 2/2004 | Takano | | 174/520 |
| 6,802,709 B1 * | 10/2004 | Mosci | | 432/119 |
| 6,948,933 B2 * | 9/2005 | Oh | | 433/81 |
| 6,981,868 B2 * | 1/2006 | Okawa et al. | | 433/81 |
| 7,008,222 B2 * | 3/2006 | Oh | | 433/81 |
| 7,448,867 B2 * | 11/2008 | Aloise et al. | | 433/81 |
| 2002/0086264 A1 | 7/2002 | Okawa et al. | | |
| 2002/0100517 A1 * | 8/2002 | Somerville et al. | | 138/148 |
| 2003/0072351 A1 * | 4/2003 | Shin | | 374/179 |
| 2003/0130658 A1 * | 7/2003 | Goble et al. | | 606/48 |
| 2004/0009452 A1 * | 1/2004 | Oh | | 433/81 |
| 2004/0173594 A1 * | 9/2004 | Weiss et al. | | 219/217 |
| 2004/0224282 A1 * | 11/2004 | Kazen et al. | | 433/81 |
| 2004/0265772 A1 * | 12/2004 | Oh | | 433/81 |
| 2005/0026106 A1 * | 2/2005 | Jefferies | | 433/81 |
| 2005/0153258 A1 * | 7/2005 | McCoy | | 433/81 |
| 2005/0282117 A1 * | 12/2005 | Aravena et al. | | 433/224 |
| 2005/0285238 A1 * | 12/2005 | Joshi et al. | | 257/673 |
| 2007/0231772 A1 * | 10/2007 | Jefferies | | 433/81 |

* cited by examiner

FIG. 13

WIRELESS RECHARGER OF COMPLETE MELTING TYPE FOR ENDODONTIC TREATMENT

TECHNICAL FIELD

The present invention relates to a filling instrument for filling gutta-percha, which is root canal filling gum, in a root canal in a dental treatment, and more particularly, to a complete melting type cordless filling instrument for endodontic treatment which uses a switching circuit to efficiently generate heat from a heating coil using a small battery without supply of external electric power, and uses a cordless handpiece to enable the filling instrument to be conveniently used.

BACKGROUND ART

In a decayed tooth treating method, which is generally used in a dental clinic, a decayed portion of a tooth is first removed using an endodontic file. When the pulp of the tooth is injured, the injured or afected pulp is also removed. Thereafter, a filler, e.g., endodontic cement or sealer, is filled in the portion of the tooth to be treated, namely, the root canal of the tooth, to seal the root canal. Finally, a prosthetic treatment is carried out for the tooth. In the root canal filling procedure, gutta-percha cones are used as a temporary filling material having an auxiliary function for enabling the filler to penetrate into the root canal and thus to seal up the root canal. Gutta-percha, which is a natural vegetable extract, has a semisolid phase at room temperature, but has the form of a solid gum when it is compressed or heated. The gutta-percha having the form of such a solid gum is called "white gutta-percha".

Generally, gutta-percha cones are prepared by adding zinc oxide, barium sulfate, wax, and pigment to gutta-percha, kneading them into a paste in a mixer, extruding the paste in the form of a sheet using rolls, cutting the sheet into pieces, and shaping the pieces into a conical structure. Thus, gutta-percha cones having various sizes can be formed. Such a gutta-percha cone is most widely used as a material for endodontic treatment that it is known as being most biologically compatible with living bodies because it is harmless to the root apexes of teeth. Gutta-percha cones, which are currently commercially available, are classified into a standardized cone and an accessory cone. The standardized cone has a shape identical to that of a dental file.

In endodontic treatment for a decayed tooth, the affected pulp of the tooth is first drilled to remove affected nerve tissues. Thereafter, a filler coats the root canal wall, in order to prevent the root canal from being further affected by a source of decay. A gutta-percha cone having a suitable size is then inserted into the root canal to fix the filler to the main and accessory portions of the root canal. In this case, it is important to bring the gutta-percha cone into complete contact with the root canal wall and apical area of the tooth.

After completion of the root canal filling procedure, the filling state in the root canal is confirmed using X-ray photography. The gutta-percha cone is then removed. For the removal of the gutta-percha cone, an excavator, an endodontic plugger, or a spreader is used in a state of being heated in flame.

The present invention relates to a gutta-percha filling instrument which applies a gutta-percha cone to a root canal wall in a dental clinic procedure, as mentioned above, such that the gutta-percha cone comes into complete contact with the root canal wall. In particular, the present invention relates to a complete heating type filling instrument for endodontic treatment which fills a root canal with a gutta-percha cone after completing melting the gutta-percha cone, thereby achieving complete filling of the root canal without waste of the gutta-percha cone. This may be explained in conjunction with Obtura II manufactured by Obtura Spartan Company. For endodontic treatment, a method for filling a root canal with gutta-percha is generally used which is carried out by filling about a ⅓ part of the root canal using a filling instrument for back-filling such as System B manufactured by Analytic Company, and then filling the remaining part of the root canal using a complete melting type filling instrument such as Obtura II manufactured by Obtura Spartan Company.

Generally, the complete melting type filling instrument, which is adapted to fill a root canal with gutta-percha, includes a handpiece, and a control box which includes a power source for supplying electric power to the handpiece, and a controller for controlling the handpiece. The handpiece, which is grasped by a doctor for endodontic treatment, is separate from the control box, and is electrically connected with the control box by a cable.

Figure 1:
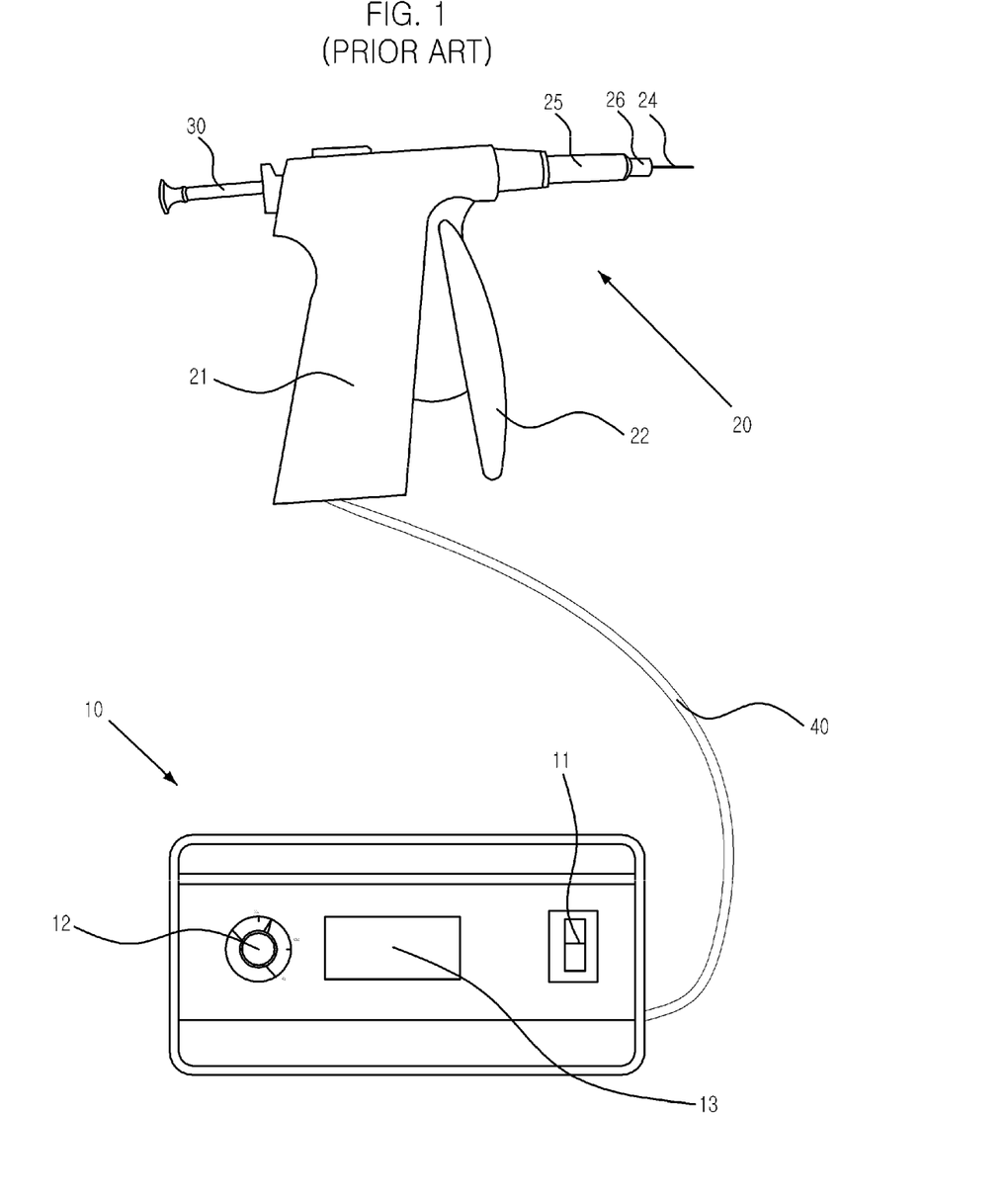
FIG. 1 is a view illustrating an example of a configuration of a conventional complete melting type filling instrument for endodontic treatment.
Figure 2:
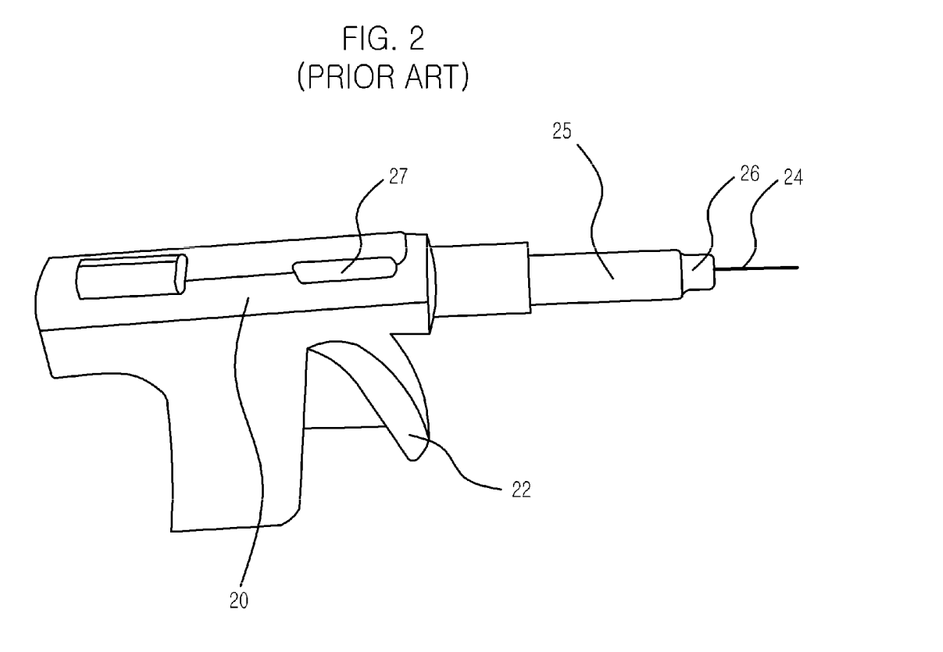
FIG. 2 is a perspective view illustrating a handpiece shown in FIG. 1.
Figure 3:
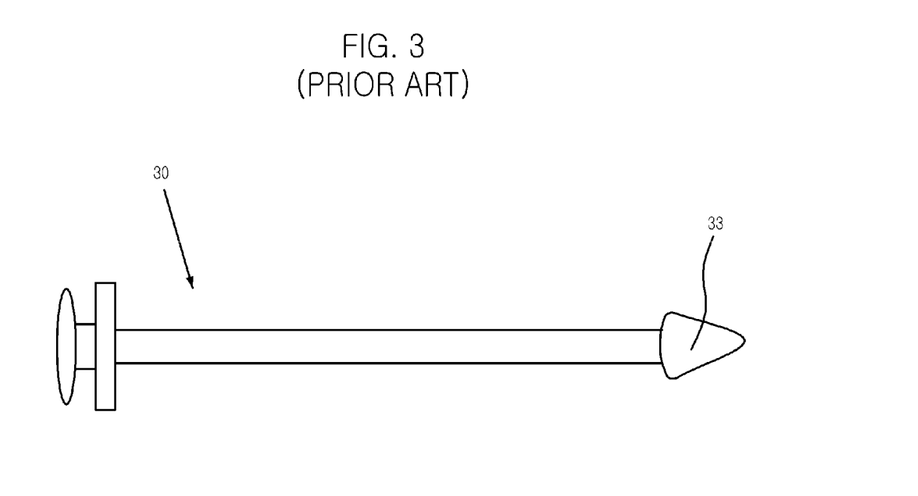
FIG. 3 is a plan view illustrating a piston which pushes gutta-percha melted in the handpiece of FIG. 2, to fill a root canal with the gutta-percha.

Hereinafter, a conventional complete melting type filling instrument for endodontic treatment will be described with reference to FIGS. 1 to 5. FIG. 1 is a view illustrating an example of a configuration of a conventional complete melting type filling instrument for endodontic treatment. FIG. 2 is a perspective view illustrating a handpiece shown in FIG. 1. FIG. 3 is a plan view illustrating a piston which pushes gutta-percha melted in the handpiece of FIG. 2, to fill a root canal with the gutta-percha.

As shown in the drawings, the conventional gutta-percha filling instrument includes a control box 10 which includes a power switch 11, a control panel 12, and a display 13 for displaying an operation state of the filling instrument. The conventional gutta-percha filling instrument also includes a handpiece 20 which includes a grip 21, a heating coil 25 for supplying heat to gutta-percha, to melt the gutta-percha, a needle-shaped injector 24 for injecting the melted gutta-percha into a root canal, a piston 30 for supplying the melted gutta-percha to the injector 24, and a filling switch 22 for driving the piston 30.

The control box 10 and handpiece 20 are connected to each other by a cable 40. Electric power required by the handpiece 20 is supplied via the cable 40.

A temperature sensor 26 is arranged at the injector 24, to sense the temperature of the injector 24. For the temperature sensor, a platinum sensor may be used which uses platinum exhibiting a variation in resistance depending on a variation in temperature, to measure a temperature based on a measured resistance of the platinum.

As shown in FIG. 2, a charging hole 27 is provided at an upper portion of the handpiece 20 of the filling instrument, to charge an upstream portion of the injector with an endodontic gutta-percha piece which has a certain standardized size. The piston 30, which is shown in FIG. 3, is arranged at the rear of the charging hole 27. Accordingly, when the operator pushes the filling switch 22, a front end 33 of the piston 30 is forwardly moved to push the charged gutta-percha. As a result, the gutta-percha is melted while passing the heating coil 25, and then, is injected into a root canal through the injector 24.

Figure 4:
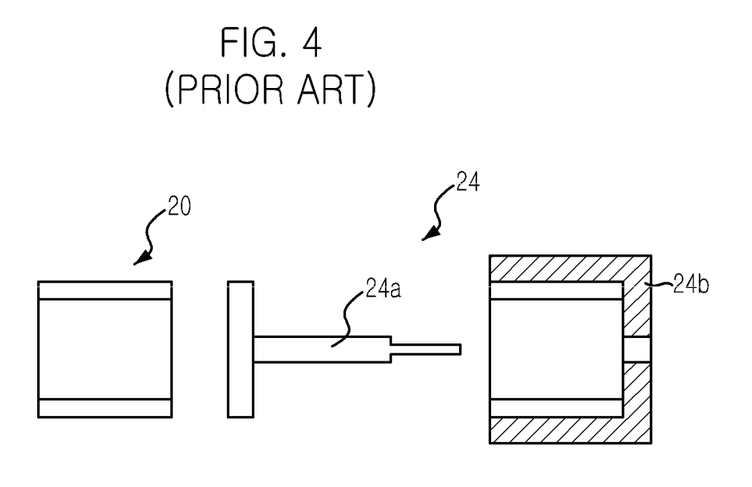
FIG. 4 is a schematic exploded view illustrating an example of an injector included in the conventional complete melting type filling instrument for endodontic treatment.
Figure 5:
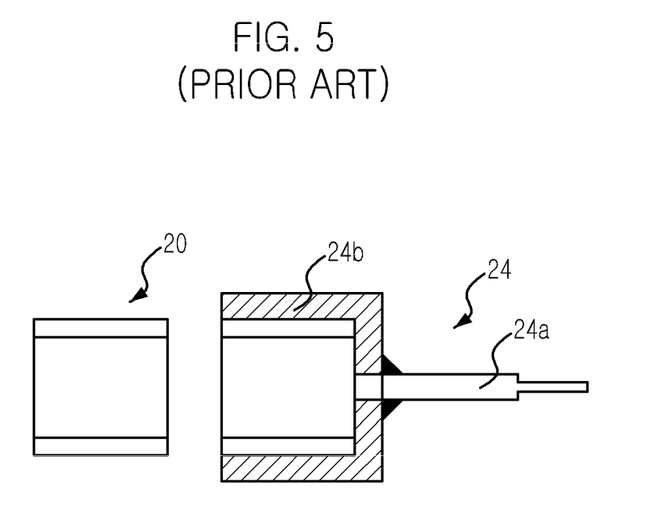
FIG. 5 is a schematic exploded view illustrating another example of the injector included in the conventional complete melting type filling instrument for endodontic treatment.

FIG. 4 is a schematic exploded view illustrating an example of the injector included in the conventional complete melting type filling instrument for endodontic treatment. FIG. 5 is a schematic exploded view illustrating another example of the injector included in the conventional complete melting type filling instrument for endodontic treatment. In the case of FIG. 4, the injector 24 includes a needle 24*a* and a cap 24*b*. The needle 24*a* is mounted to a body of the injector 24 by the cap 24*b*.

Generally, operators use a needle after bending the needle. When it is desired to perform a task in a direction opposite to the bending direction of the bent needle, the operator must re-bend the needle in the opposite direction. Otherwise, the operator must perform operations of unfastening the cap, turning the needle such that the bending direction of the needle is reversed, and re-fastening the cap to fix the needle. However, it is difficult to easily perform the task because the body and needle of the injector have a temperature of about 200° C. In addition, there is a possibility that the needle 24a may be easily broken after being bent several times in opposite directions because the material thickness of the needle 24a is small. Furthermore, the filler may be leaked because there is no seal member provided at the injector.

In the case of the other conventional injector, as shown in FIG. 5, a needle 24a of the injector 24 is welded to one end of a cap 24b. In this case, when it is necessary to reversely change the bending direction of the needle 24a, the needle 24a must be re-bent in the reverse direction because the needle 24a is in a state of being fixed to the cap 24b. For this reason, the needle 24a may be easily broken.

The above-mentioned conventional gutta-percha filling instrument for endodontic treatment has a problem that there is inconvenience in carrying the filling instrument because the control box 10 and handpiece 20 are separate from each other. Also, there are problems of high manufacturing costs and a complex manufacturing procedure because it is necessary to additionally provide the temperature sensor for sensing the temperature of the heating coil.

Moreover, there is a problem that malfunction or failure occurs due to twisting, bending, or breaking of the cable connecting the control box and handpiece. Also, there is a problem that the operation range is limited because the movement range of the handpiece is limited by the cable. The view of the operator is also limited by the cable.

In addition, there is a problem that the concentration of the operator upon the operation may be degraded because the operator should additionally control the control box which is separate from the handpiece.

DETAILED DESCRIPTION OF THE INVENTION

Technical Problem

Therefore, the present invention has been made in view of the above problems, and it is an object of the present invention to provide a complete melting type cordless filling instrument for endodontic treatment which uses a switching circuit enabling the filling instrument to be operable using a miniature dry battery adapted to supply DC power.

Another object of the present invention is to provide a complete melting type cordless filling instrument for endodontic treatment which includes an injector including a body, a needle rotatably mounted to the body, and a gasket fitted around a mounting portion of the needle to the body, thereby being capable of preventing leakage of a filler around the mounting portion of the needle, and enabling the needle, which has been bent once, to be used without re-bending thereof when it is necessary to reverse the bending direction of the needle, in accordance with rotation of the needle.

Technical Solution

In accordance with an aspect of the present invention, the above and other objects can be accomplished by the provision of a complete melting type cordless filling instrument for endodontic treatment comprising: a body in which a battery for supplying DC power is arranged; a heater which is arranged at a front end of the body, to heat and melt gutta-percha; an injector which is mounted to the body in front of the heater, to discharge the melted gutta-percha; a charging part which is provided at the body, to charge the gutta-percha in the body; a feeding member which feeds the gutta-percha charged in the body at the charging part to the injector; a filling switch which turns on the heater; and a control circuit which is installed in the body, to control a temperature of the heating core and an operation of the heating core, the control circuit including the filling switch, and a switching circuit adapted to very efficiently maintain electrical energy supplied from the battery.

The body may be provided with a grip which extends downwardly such that an operator can grasp the grip. The filling switch may be mounted to the body in front of the grip, to enable the operator to easily operate the filling switch by the fingers.

The charging part may include a charging hole formed at the body. The feeding member may include a piston which has a front end arranged at the rear of the charging hole, and is forwardly moved through the charging hole when the filling switch is pressed, to cause the front end of the piston to push the gutta-percha.

An operation condition setting button and a display may be integrally installed on the body, to set an operation condition.

The heater may include heater bases which are different metals, respectively, a heating coil which is wound around one of the heater bases, and is made of a metal different from the metals of the heater bases, and a temperature measurer which measures a temperature of the heating coil.

The temperature measurer may include a thermally-isolated temperature detector, electric wires which connect the temperature detector and the heating coil, and a circuit which measures a thermal electromotive force generated at the electric wires, and calculates the temperature of the heating coil, based on the measured thermal electromotive force.

The electric wires may include a first electric wire connected to one end of the heating coil, and a second electric wire connected to the other end of the heating coil. The first electric wire may be made of a metal identical to the metal of the heating coil. The second electric wire may be made of a metal different from the metal of the heating coil. The first electric wire may have an electric resistance considerably lower than an electric resistance of the heating coil. The metal of the second electric wire may generate a thermal electromotive force lower than a thermal electromotive force generated by the metal of the first electric wire. The heating coil and the first electric wire may be made of nickel, whereas the second electric wire may be made of copper. The heating coil may have a resistance of 0.2 to 1.0Ω.

The body may be made of an insulator, to prevent heat from being transferred to a grip which is mounted to the body such that an operator can grasp the grip. The body may be provided with an insulating hole, to provide an insulating effect to the body.

The switching circuit may be a synchronous type buck converter switching circuit which includes two switches controlled to be alternately opened and closed, an inductor connected to one of the switches in parallel, and a resistor connected to the inductor in series.

The resistor may include an element having a positive temperature coefficient. The battery may be a rechargeable battery.

Advantageous Effects

In accordance with the present invention, a cordless gutta-percha filling instrument for endodontic treatment can be manufactured using a switching circuit, and a heating coil having a positive temperature coefficient, because it is possible to very efficiently generate heat from the heating coil using a DC power source.

In accordance with the present invention, it is also possible to maximize the convenience of the user because the gutta-percha filling instrument is of a cordless type.

In accordance with the present invention, measurement of a thermal electromotive force is achieved using different metals, to measure the temperature of the heating coil. Accordingly, it is unnecessary to use a separate temperature sensor. Thus, simple manufacture and a reduction in manufacturing costs can be achieved.

BRIEF DESCRIPTION OF THE DRAWINGS

The above and other objects, features and other advantages of the present invention will be more clearly understood from the following detailed description taken in conjunction with the accompanying drawings, in which.

BEST MODE

Hereinafter, a complete melting type cordless filling instrument for endodontic treatment according to an exemplary embodiment of the present invention will be described with reference to FIGS. 6 to 12.

Figure 6:
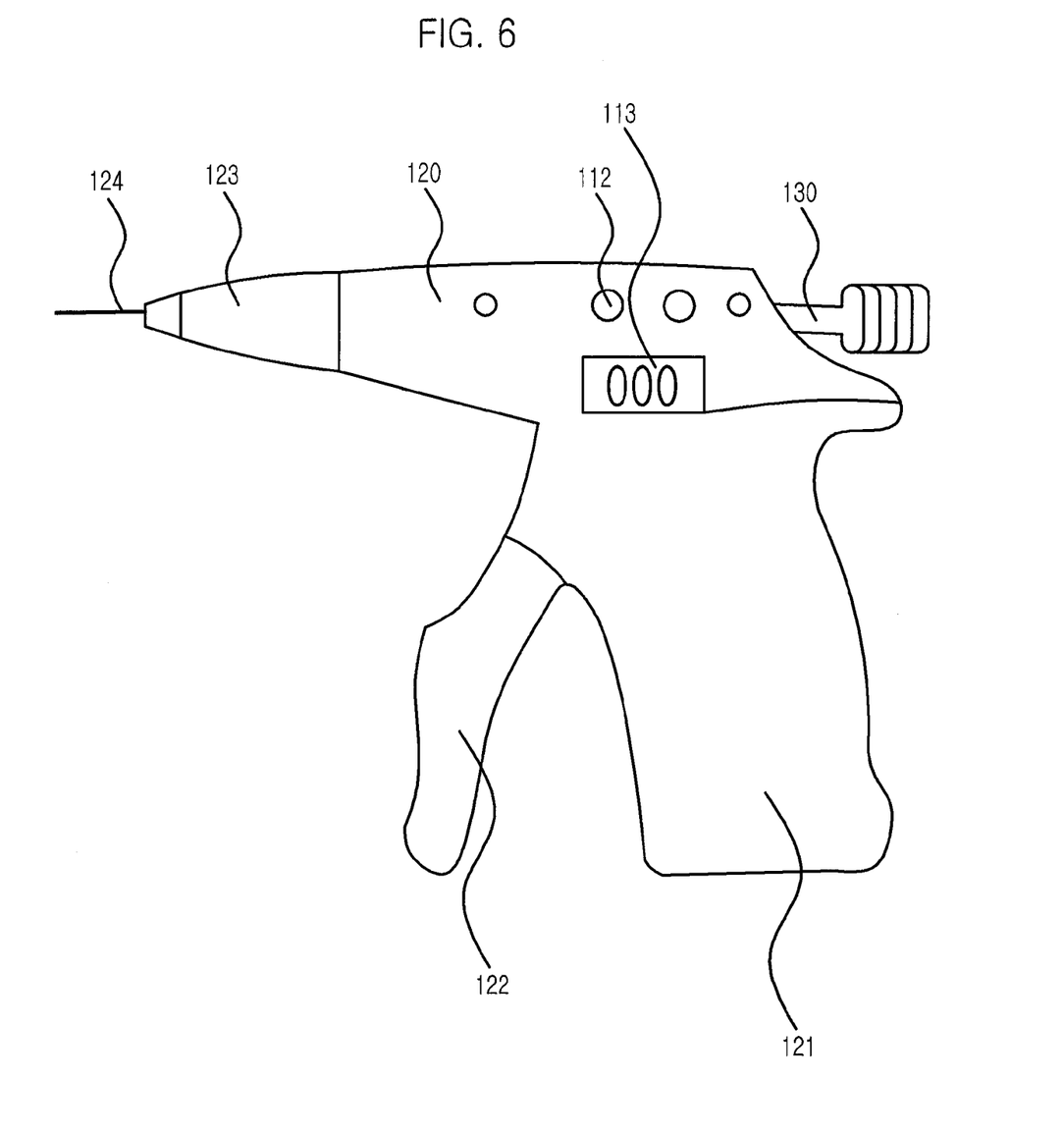
FIG. 6 is a side view illustrating a complete melting type cordless filling instrument for endodontic treatment according to an exemplary embodiment of the present invention.
Figure 7:
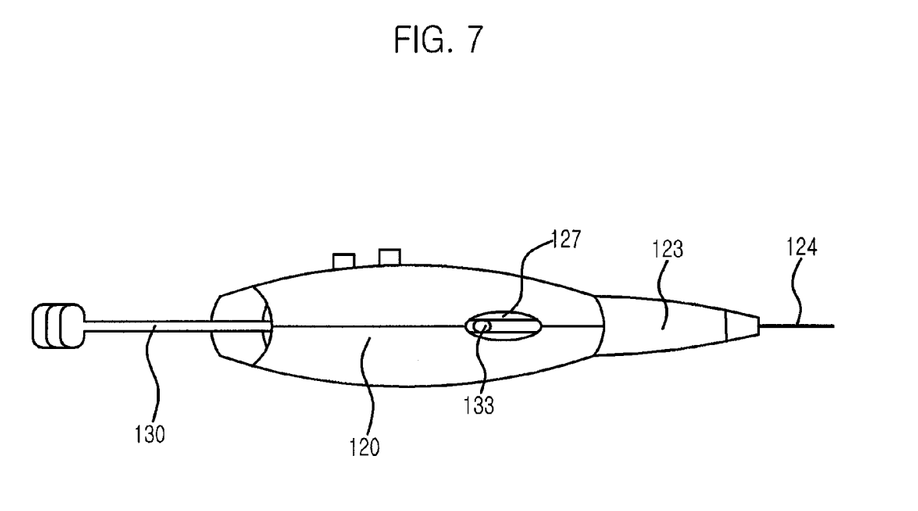
FIG. 7 is a plan view corresponding to FIG. 6.

FIG. 6 is a side view illustrating a complete melting type cordless filling instrument for endodontic treatment according to an exemplary embodiment of the present invention. FIG. 7 is a plan view corresponding to FIG. 6. As shown in the drawings, the complete melting type cordless filling instrument for endodontic treatment according to the present invention includes a body 120, a heater 123, an injector 124, a charging part 127, a feeding member 130, a filling switch 122, and a control circuit (not shown).

A power source, which supplies DC power, is arranged in the body 120. The body 120 includes a grip 121 which extends downwardly. The filling switch 122 is mounted to the body 120 in front of the grip 121, to enable the operator to operate the filling switch 122 by the fingers. An operation condition setting button 112 is arranged on a desired portion of the body 120, to set a desired operation condition of the filling instrument. A display 113 is also arranged on a desired portion of the body 120, to display an operation state of the filling instrument. A charging hole is formed at the body 120, as the charging part 127 which will be charged with gutta-percha. It is preferred that the charging hole 127 be formed at a top portion of the body 120, in order to achieve smooth charging of gutta-percha and smooth feeding of the charged gutta-percha to the injector 124.

The feeding member 130 is adapted to feed the charged gutta-percha to the injector 124. The feeding member 130 is constituted by a piston which is slidable in accordance with operation of the filling switch 122, to push the charged gutta-percha.

Hereinafter, the constituent elements of the complete melting type cordless filling instrument for endodontic treatment according to the present invention, and functions and effects thereof will be described with reference to the annexed drawings.

Figure 8:
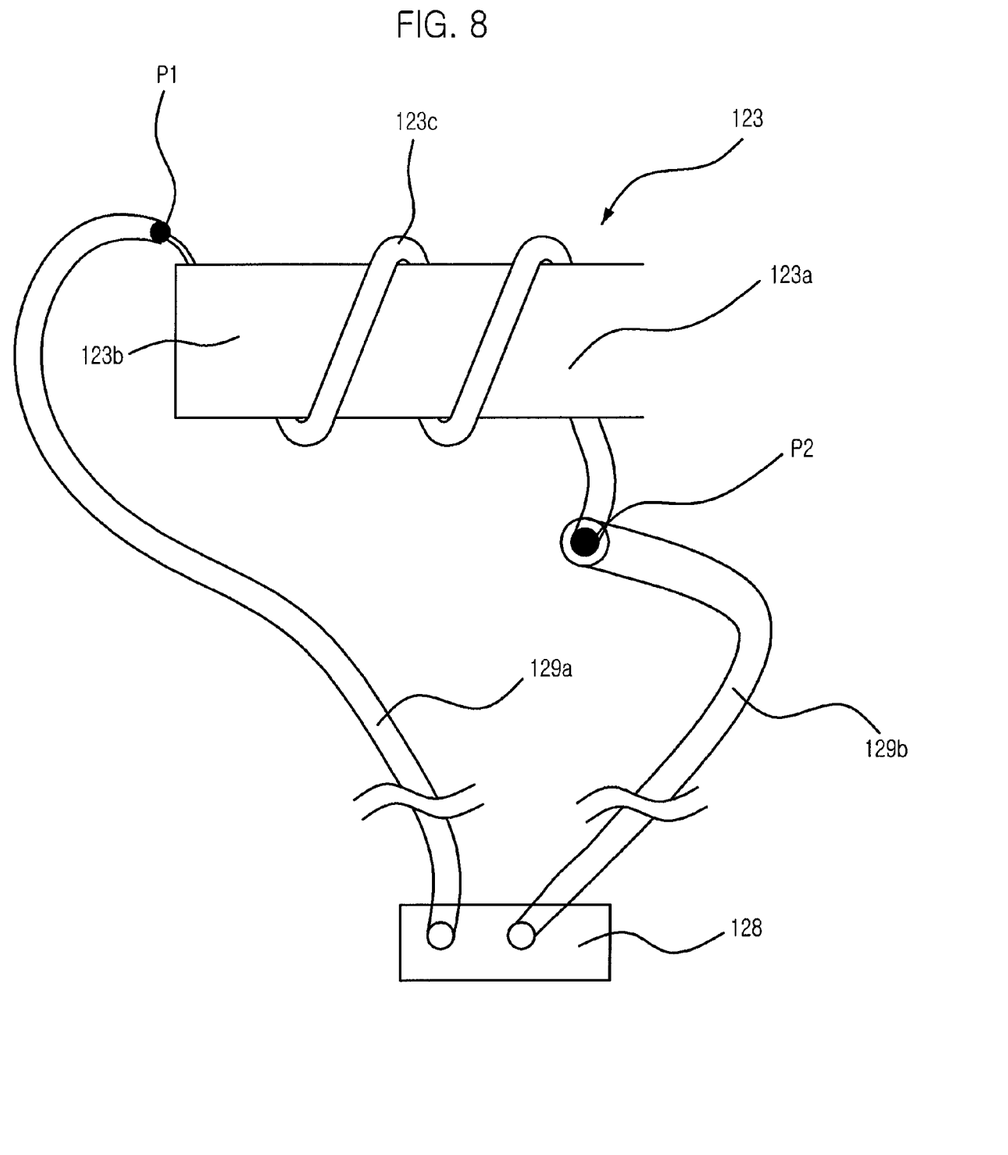
FIG. 8 is a schematic view illustrating a heater and a temperature detector.

FIG. 8 is a schematic view illustrating the heater and a temperature detector. The heater 123 includes heater bases 123a and 123b which are made of different metals, respectively, and a heating coil 123c which is wound around one of the heater bases 123a and 123b, and is made of a metal different from the metals of the heater bases 123a and 123b.

The heating coil 123c is connected to a temperature detector 128 via electric wires 129a and 129b. The temperature detector 128 is maintained at room temperature, whereas the heating coil 123c has the same temperature as the heater 123 and the gutta-percha heated by the heater 123. Accordingly, there is a temperature difference between the heating coil 123c and the temperature detector 128. By virtue of a Seebek effect caused by the temperature difference, a thermal electromotive force is generated between contacts P1 and P2. As a result, current flows. Since the thermal electromotive force is proportional to temperature, it is possible to detect the temperature of the heater 123 by measuring the thermal electromotive force causing current to flow through the electric wires 129a and 129b.

A first one of the electric wires 129a and 129b, namely, the first electric wire 129a, is connected to one end of the heating coil 123c, whereas the second electric wire 129b is connected to the other end of the heating coil 123c. The first electric wire 129a is made of the same metal as the heating coil 123c, but has an electric resistance considerably lower than that of the heating coil 123c. On the other hand, the second electric wire 129b is made of a metal which is different from that of the first electric wire 129a, and generates a thermal electromotive force higher than that of the first electric wire 129a. In an embodiment of the present invention, the first electric wire 129a is made of nickel (thermal electromotive force on the basis of platinum: −1.43 mV/100° C.), whereas the second electric wire 129b is made of copper (thermal electromotive force on the basis of platinum: 0.75 mV/100° C.). The reason why the two electric wires are implemented using different metals is to prevent the electric wires from being connected in reverse series when measurement of a thermal electromotive force is carried out, and thus, to enable a temperature detection using measurement of a thermal electromotive force.

Figure 9:
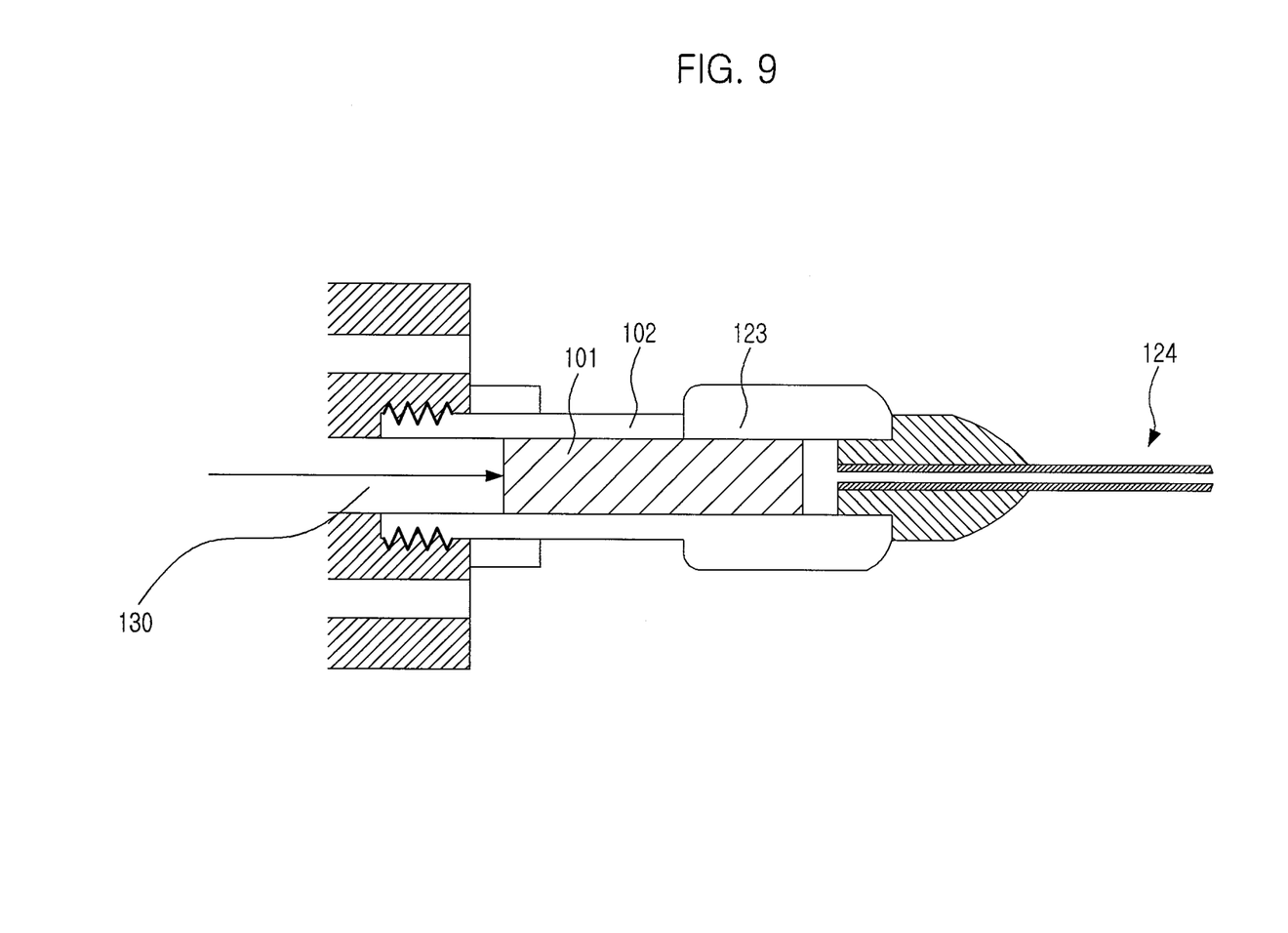
FIG. 9 is a schematic cross-sectional view illustrating a gutta-percha charging part and an injector shown in FIG. 6.

FIG. 9 is a schematic cross-sectional view illustrating the gutta-percha charging part and injector shown in FIG. 7. As shown in the drawing, the injector 124 is connected to one end of the heater 123. The heater 123 is connected to a gutta-percha passage 102 defined in the body 120. Gutta-percha 101 is charged in the gutta-percha passage 102 through the charging hole 127. The charged gutta-percha 101 is forwardly pushed by the piston 130 which is operatively connected to the filling switch 122. At this time, the gutta-percha 101 is fed into the injector 124 via the gutta-percha passage 102 and heater 123. The gutta-percha 101, which is in a solid state, is melted by the heater 123 during the feeding procedure. As a result, the gutta-percha 101 is supplied to the injector 124 in a melted state. In this case, although the gutta-percha 101 is melted by the heater 123, the rear portion of the gutta-percha 101 is maintained in a relatively solid state. Accordingly, the gutta-percha 101 is easily pushed by the piston 130.

The operative connection of the piston 130 to the filling switch 122 may be implemented using various mechanical or electronic devices, as will be appreciated by those skilled in the art.

Figure 10:
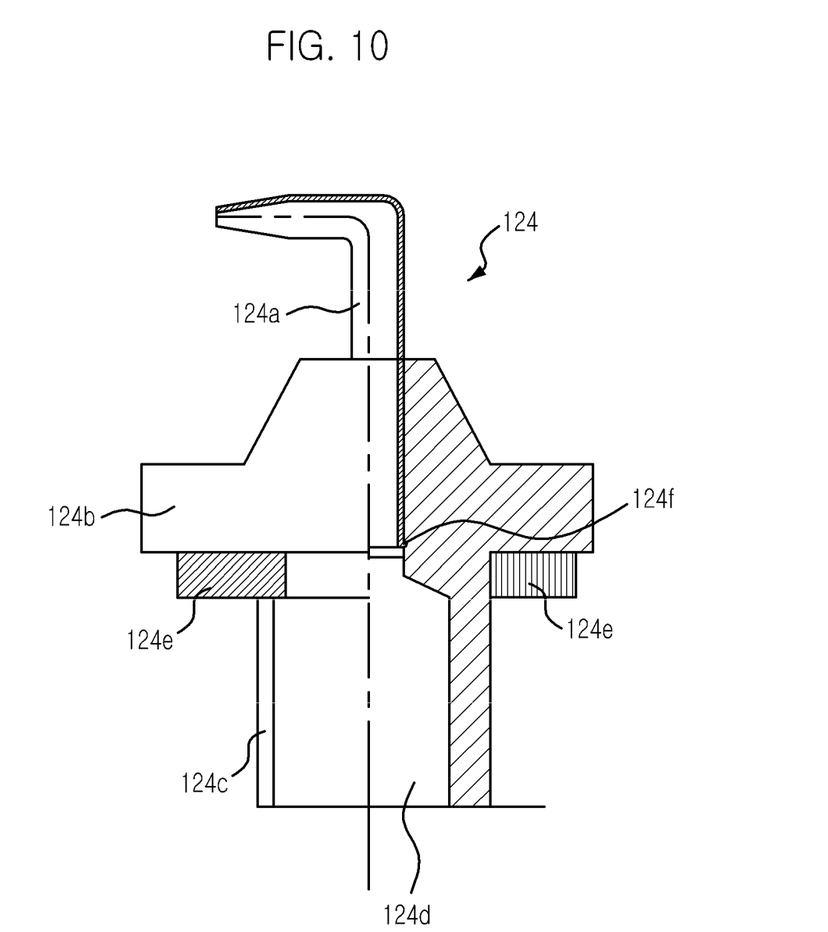
FIG. 10 is a schematic cross-sectional view of another embodiment of the injector shown in FIG. 6, illustrating an injector including a needle which is rotatable, and is bent by a predetermined angle.

FIG. 10 is a schematic cross-sectional view of another embodiment of the injector shown in FIG. 6, illustrating an injector including a needle which is rotatable, and is bent by a predetermined angle. As shown in the drawing, the injector 124 included in the complete melting type cordless filling instrument for endodontic treatment according to the present invention includes a needle 124a, an injector body 124b, a threaded portion 124c, a gutta-percha inlet 124d, and a seal member 124e.

The needle 124a is adapted to inject melted gutta-percha to a desired position. The needle 124a is bent by a predetermined angle, in order to enable the operator to conveniently perform a desired task. The needle 124a is constituted by a pipe made of silver alloy coupled with copper alloy or SUS. The needle 124a has a diameter of about 0.9 mm at one end thereof, namely, a coupling end thereof. Preferably, the needle 124a has a diameter varying from about 0.5 to about 0.9 mm at the other end thereof so that it is conveniently used for dental treatment. The needle 124a is rotatably coupled to the injector body 124b. For the rotatable coupling, the needle 124a is provided, at one end thereof, with an annular coupling protrusion 124f having a diameter larger than the diameter of the needle 124a. Also, the injector body 124b is formed with an annular groove corresponding to the annular coupling protrusion 124f. The annular coupling protrusion 124f of the needle 124a is fitted in the annular groove of the injector body 124b such that a predetermined gap is defined therebetween, to allow the annular coupling protrusion 124f to be 360° rotatable around the annular groove without being loosened. Accordingly, the operator can reliably perform a desired treatment.

The injector body 124b has a hexagonal rod shape so that it can be easily coupled to the body of the filling instrument. The seal member 124e is adapted to prevent gutta-percha of a high temperature from being leaked. The seal member 124e is constituted by a gasket which is resistant to high temperatures. The seal member 124e is fitted around the threaded portion 124c of the injector body 124b at the front end of the threaded portion 124c.

In accordance with the above-described configuration, high-temperature gutta-percha melted by the heater 123 is introduced into the injector 124 through the gutta-percha inlet 124d. The introduced gutta-percha can be injected to a desired place while being prevented from being leaked by the gasket 124e. When the operator desires to use the injector 124 in a direction reverse to the bending direction of the needle 124a, he can conveniently use the injector 124 after rotating the needle 124a by a desired angle.

Figure 11:
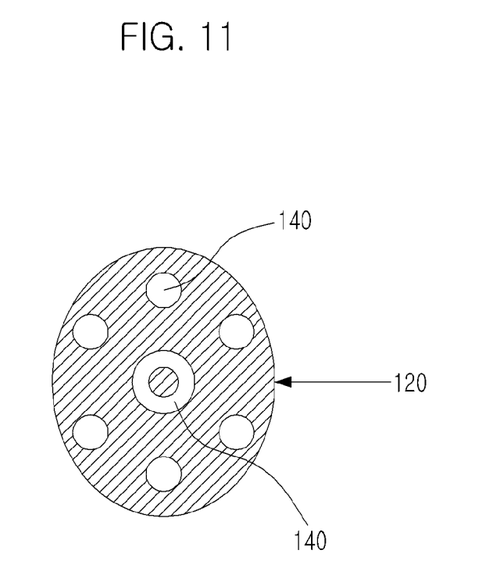
FIG. 11 is a sectional view illustrating the case in which an insulating hole is formed in a body of the complete melting type cordless filling instrument for endodontic treatment according to the present invention, in order to achieve an enhancement in insulating function.

FIG. 11 is a sectional view illustrating the case in which an insulating hole is formed in the body of the complete melting type cordless filling instrument for endodontic treatment according to the present invention, in order to achieve an enhancement in insulating function.

In accordance with this embodiment, the body 120 is made of an insulator, in order to prevent heat from being easily transferred to the grip 121 which is grasped by the operator. For an increased insulation effect, as shown in the drawing, an insulating hole 140 is formed in the body 120. Accordingly, it is possible to securely prevent heat from being transferred to the operator. If heat is transferred to the operator, the operator may erroneously perform a task. This situation may be very dangerous to the patient. Accordingly, it is important to provide an insulating structure such as the above-described insulating hole. Such an insulating structure is also important that it is possible to enable the cordless instrument to maintain a high efficiency, and thus, to reduce loss of heat.

Figure 12:
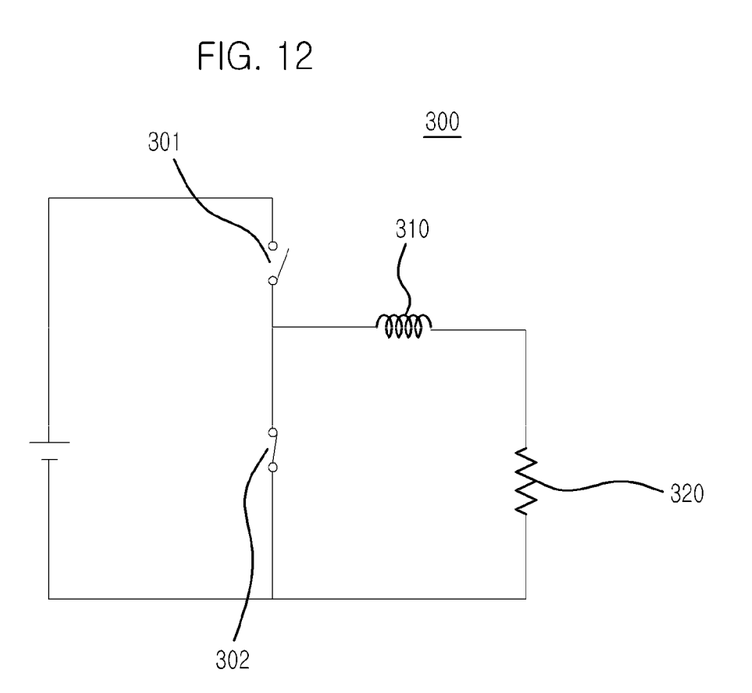
FIG. 12 is a circuit diagram illustrating a switching circuit for maximizing the efficiency of a power source in accordance with an embodiment of the present invention.

FIG. 12 is a circuit diagram illustrating a switching circuit for maximizing the efficiency of the power source in accordance with an embodiment of the present invention.

As shown in FIG. 12, in the illustrated embodiment, a cordless instrument is implemented using a DC power source. For this implementation, a synchronous type buck converter 300 is used.

That is, the buck converter 300 includes two switches 301 and 302 which are controlled to be alternately opened and closed. An inductor 310 is connected to one switch 302 in parallel. A resistor 320 is connected to the inductor 310 in series.

The resistor 320 may be used as a heating coil. The resistor 320 is constituted by an element having a positive temperature coefficient (PTC).

Figure 13:
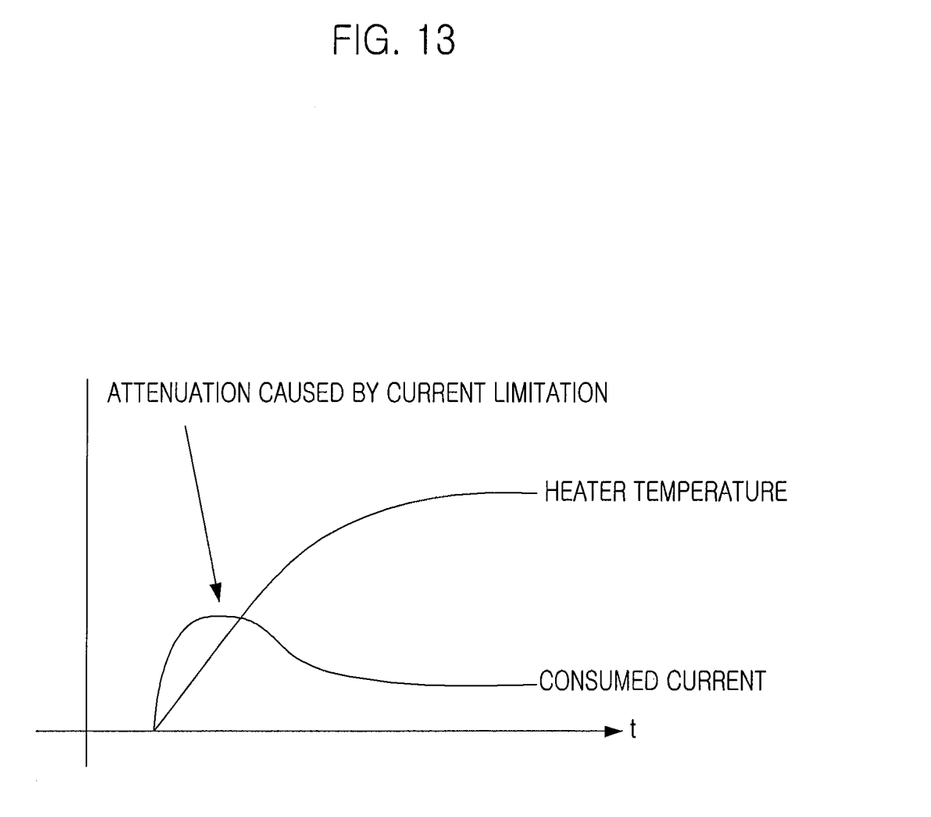
FIG. 13 is a graph depicting the relation between the current consumed by the switching circuit of FIG. 12 and the temperature of a heat generating element.

FIG. 13 is a graph depicting the relation between the current consumed by the switching circuit of FIG. 12 and the temperature of a heat generating element.

In particular, the graph of FIG. 13 depicts the relation between the time-based consumed current and the temperature of the heat generating element in the case in which the resistor 320 is constituted by an element having a PTC.

Referring to the graph, it can be seen that it is possible to reduce the consumption of current using the element having a PTC as a heat generating element. Thus, the above-described switching circuit is suitably used in a cordless appliance requiring a high efficiency, as in the present invention.

In the illustrated embodiment, a rechargeable battery is used. Accordingly, since the battery is rechargeable, it is possible to prevent stoppage of treatment caused by shortage of battery power during execution of the treatment. It is also possible to eliminate inconvenience caused by frequent replacement of dry batteries.

Hereinafter, the functions and effects of the above-described present invention will be described.

The present invention is implemented in the form of a cordless type unit using no separate power source because the control box is completely built in the handpiece. Accordingly, it is possible to maximize the use convenience of the user.

In accordance with the present invention, a switching circuit is used to achieve very-efficient supply of heat using a DC power source. That is, when the heat generating element of the heater is directly connected to a power source having a certain voltage without using the switching circuit, a great increase in current occurs because the resistance of the heat generating element is very small. For this reason, the current flowing through the heater may be larger than the allowable current of the battery. As the current increases, a degradation in efficiency and an increase in consumption of power occur. As a result, the usable time of the battery is reduced. In severe cases, it may be impossible to use the battery. However, when the switching circuit is used, as in the present invention, it is possible to control the time, for which current flows, namely, current limiting time, and thus, to accumulate energy. That is, it is possible to accumulate electrical energy in the inductor of the switching circuit. Accordingly, an increase in the efficiency of the battery, and thus, an increase in the use time of the battery, can be achieved.

It was experimentally confirmed that, when a 3.7 V DC power source having an internal resistance of $0.08\Omega$ is directly connected to a heating coil of $0.2\Omega$, current of 14 A flows which considerably exceeds allowable current of 6 A, so that it is impossible to use the circuit. In this case, it was also confirmed that the use time of the battery is about 4 minutes which is very short, and the temperature of the heat generating element increases. However, when a switching circuit using a synchronous type buck converter was used, as in the present invention, current was reduced, and was maintained at about 1.7 A, even through consumption of initial current was large, as shown in the graph of FIG. 13. As a result, the continuous use time of the battery was one hour or more. Also, the temperature of the heating coil was maintained constant.

As apparent from the above description, in accordance with the present invention, a cordless gutta-percha filling instrument for endodontic treatment capable of using a miniature battery can be manufactured using a switching circuit which realizes a high efficiency.

In accordance with the present invention, control elements such as the display 113 and operation condition setting button 112 are completely installed on the body 120. Accordingly, the operator can concentrate upon an operation. It is also possible to conveniently carry the instrument.

In accordance with the present invention, measurement of a thermal electromotive force is achieved using different metals, to measure the temperature of the heating coil. Accordingly, it is unnecessary to use a separate temperature sensor. Thus, simple manufacture and a reduction in manufacturing costs can be achieved.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

What is claimed is:

1. A complete melting type cordless filling instrument for endodontic treatment comprising:
    a body in which a battery for supplying DC power is arranged and having a grip which is mounted to the body such that an operator can grasp the grip;
    a heater which is arranged at a front end of the body, to heat and melt gutta-percha;
    an injector which is mounted to the body in front of the heater, to discharge the melted gutta-percha;
    a charging part which is provided at the body, to charge the gutta-percha in the body;
    a feeding member which feeds the gutta-percha charged in the body at the charging part to the injector;
    a filling switch which operates the feeding member to feed the gutta-percha to the injector; and
    a control circuit which is installed in the body, to control a temperature of the heater and an operation of the heater, the control circuit including a switching circuit adapted to efficiently maintain electrical energy supplied from the battery and the filling switch,
    wherein the body comprises an insulator, the insulator comprising a plurality of insulating holes longitudinally-extending through an interior of the insulator to reduce heat transfer to the grip;
    wherein the injector includes:
        an injector body which includes a gutta-percha inlet formed through the injector body, and a threaded coupling portion formed on an outer peripheral surface of the injector body;
        a needle which is rotatably mounted to the injector body, and is made of a bendable material wherein the needle includes:
            a cylindrical pipe;
            an annular protrusion formed at one end of the cylindrical pipe such that the annular protrusion has a diameter larger than a diameter of the cylindrical pipe, to enable the cylindrical pipe to be rotatably coupled to the injector body; and
            a tapered end formed at the other end of the cylindrical pipe; and
        a seal member which is mounted between the injector body and the body, to prevent the gutta-percha from being leaked;
    wherein the heater includes:
        a heating coil formed of an element having a positive temperature coefficient (PTC); and
        a temperature measurer including:
            a thermally-isolated temperature detector;
            a first electric wire connected to the temperature detector and one end of the heating coil;
            a second electric wire connected to the temperature detector and the other end of the heating coil, wherein (i) one of the first and second electric wires is formed by a same metal as the heating coil and has an electric resistance less than an electric resistance of the heating coil, and (ii) the first and second electric wires are formed by different metals; and
            a circuit configured to measure a thermal electromotive force generated at the first and second electric wires, and to calculate a temperature of the heating coil, based on the measured thermal electromotive force; and
    wherein the switching circuit includes a synchronous type buck converter including two switches and an energy storing element, and is positioned between the battery and the heating coil, wherein the heating coil is connected to the energy storing element in series.

2. The complete melting type cordless filling instrument for endodontic treatment as set forth in claim 1, wherein:
    the needle includes a pipe which is made of silver alloy coupled with one of copper alloy and SUS;
    the needle has a diameter of about 0.9 mm at one end of the needle at which the needle is mounted to the injector body; and
    the needle has a tapered end at the other end of the needle, the tapered end having a diameter varying from about 0.5 to about 0.9 mm.

3. The complete melting type cordless filling instrument for endodontic treatment as set forth in claim 1, wherein:

the filling switch is mounted to the body in front of the grip, to enable the operator to easily operate the filling switch by the fingers.

4. The complete melting type cordless filling instrument for endodontic treatment as set forth in claim 1, wherein:
the charging part includes a charging hole formed at a top portion of the body; and
the feeding member includes a piston which has a front end arranged at the rear of the charging hole, and is forwardly moved through the charging hole when the filling switch is pressed, to cause the front end of the piston to push the gutta-percha.

5. The complete melting type cordless filling instrument for endodontic treatment as set forth in claim 1, further comprising:
an operation condition setting button and a display which are integrally installed on the body, to set an operation condition.

6. The complete melting type cordless filling instrument for endodontic treatment as set forth in claim 1, wherein the metal of the second electric wire generates a thermal electromotive force lower than a thermal electromotive force generated by the metal of the first electric wire.

7. The complete melting type cordless filling instrument for endodontic treatment as set forth in claim 1, wherein:
the heating coil and the first electric wire are made of nickel; and
the second electric wire is made of copper.

8. The complete melting type cordless filling instrument for endodontic treatment as set forth in claim 1, wherein the heating coil has a resistance of 0.2 to 1.0Ω.

9. The complete melting type cordless filling instrument for endodontic treatment as set forth in claim 1, wherein:
the synchronous type buck converter includes the two switches controlled to be alternately opened and closed, and an inductor connected to one of the switches in parallel; and
the heating coil is connected to the inductor in series.

10. The complete melting type cordless filling instrument for endodontic treatment as set forth in claim 1, wherein the battery is a rechargeable battery.

11. The complete melting type cordless filling instrument for endodontic treatment as set forth in claim 1, wherein the annular protrusion of the needle is fitted into an annular groove of the injector body to allow the annular coupling protrusion to be 360° rotatable around the annular groove without being loosened.

\* \* \* \* \*